United States Patent [19]

Moser et al.

[11] Patent Number: 4,919,709

[45] Date of Patent: Apr. 24, 1990

[54] N-(1'-METHYL-2'-METHOXYETHYL)-N-CHLOROACETYL-2,6-DIMETHYLANILINE AS HERBICIDE

[75] Inventors: Hans Moser, Magden; Christian Vogel, Binningen, both of Switzerland

[73] Assignee: Ciba-Geigy Corporation, Ardsley, N.Y.

[21] Appl. No.: 679,438

[22] Filed: Dec. 7, 1984

Related U.S. Application Data

[63] Continuation-in-part of Ser. No. 570,709, Jan. 13, 1984, abandoned.

[30] Foreign Application Priority Data

Jan. 25, 1983 [CH] Switzerland ............................ 399/83

[51] Int. Cl.$^5$ ............................................ A01N 37/22
[52] U.S. Cl. ...................................... 71/118; 564/211; 564/214
[58] Field of Search ................... 564/214, 211; 71/118

[56] References Cited

U.S. PATENT DOCUMENTS

| | | | |
|---|---|---|---|
| 3,028,430 | 4/1962 | Gillingham | 564/304 X |
| 3,576,854 | 4/1971 | Felder et al. | 514/304 X |
| 3,952,056 | 4/1976 | Vogel | 564/214 |
| 3,969,397 | 7/1976 | Kaiser et al. | 564/304 X |
| 4,168,965 | 9/1979 | Vogel et al. | 564/214 X |
| 4,345,938 | 8/1982 | Alt | 564/214 X |

OTHER PUBLICATIONS

Fieser et al., "Reagents for Organic Synthesis", vol. 6, p. 64 (1977).

Wagner et al., "Synthetic Organic Chemistry", pp. 155–156 (1963).

Burger, "Medicinal Chemistry", 3rd Ed., Part I, pp. 81–82 and 100–103 (1970).

*Primary Examiner*—Robert V. Hines
*Attorney, Agent, or Firm*—Bruce M. Collins; Edward McC. Roberts

[57] ABSTRACT

The optically active isomer of S(-)-N-(1'methyl-2'-methoxyethyl)-N-chloroacetyl-2,6-dimethylaniline has improved action against problem weeds over the racemic mixture of isomers.

1 Claim, No Drawings

N-(1'-METHYL-2'-METHOXYETHYL)-N-CHLOROACETYL-2,6-DIMETHYLANILINE AS HERBICIDE

REFERENCE TO RELATED APPLICATION

This is a continuation-in-part of our application Ser. No. 570,709, filed Jan. 13, 1984, now abandoned.

The present invention relates to the isomer of N-(1'-methyl-2'-methoxyethyl)-N-chloroacetyl-2,6-dimethylaniline having a S(−) configuration, to a process for the preparation thereof, to herbicidal compositions which contain this isomer as active ingredient, and to the use of said isomer for controlling weeds and regulating plant growth.

N-(1'-Methyl-2'-methoxyethyl)-N-chloroacetyl-2,6-dimethylaniline is already known as a racemate. This mixture of isomers, its preparation and the use thereof as plant regulator and herbicide is described e.g. in U.S. Pat. No. 3,952,056.

In the molecule of N-(1'-methyl-2'-methoxyethyl)-N-chloroacetyl-2,6-dimethylaniline of the formula I

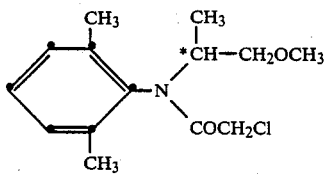

there is present one chiral carbon atom(*).

When N-(1'-Methyl-2'-methoxyethyl)-N-chloroacetyl-2,6-dimethylaniline is prepared by methods, known up to now, this compounds is obtained as mixture of enantiomers. Up to now, nothing is known about the biological activity of the individual enantiomers.

It has been found that the isomer of N-(1'-methyl-2'-methoxyethyl)-N-chloroacetyl-2,6-dimethylaniline having the S(−)configuration has a substantially better herbicidal action than the previously known racemic mixture.

Accordingly the present invention relates to the isomers having a negative rotation of N-(1'-methyl-2'-methoxyethyl)-N-chloroacetyl-2,6-dimethylaniline with the S-configuration. This isomer according to the invention will be referred to as S(−)-N-(1'-methyl-2'-methoxyethyl)-N-chloroacetyl-2,6-dimethylaniline throughout the specification.

The invention refers also to a process for the preparation of the isomer of N-(1-methyl-2'-methoxyethyl)-N-chloroacetyl-2,6-dimethylaniline with S(−)-configuration, which process comprises reducing S(−)-N-(2,6-dimethylphenyl)alanine of the formula II

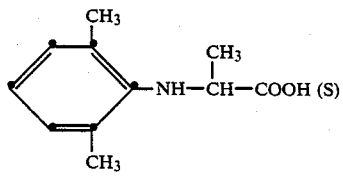

to S(−)-N-(1-methyl-2'-hydroxyethyl)-2,6-dimethylaniline of the formula III

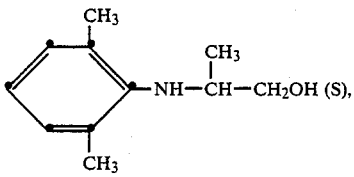

chloracylating this compound at the nitrogen atom and subsequently etherifying the resulting S(+)-N-(1'-Methyl-2'-hydroxyethyl)-N-chloroacetyl-2,6-dimethylaniline of the formula IV

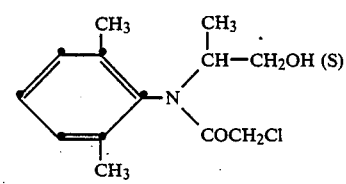

in presence of a strong acid with methanol at the 2'-hydroxy group.

The starting S(−)-N-(2'-6-dimethylphenyl)alanine may be obtained by converting racemic N-(2'-6-dimethylphenyl)-alanine, in a suitable solvent, with an optically active base into diastereomeric salts, separating said diastereomeric salts by fractional crystallisation and then cleaving them.

The racemic N-(2,6-dimethylphenyl)-alanine may itself be obtained by reacting 2,6-dimethylaniline, in the presence of a base, with a 2-halopropionic acid ester and subsequently saponifying the reaction product.

Examples of suitable optically active bases are: S(+)-2-amino-1-butanol, R(−)-2-amino-1-butanol. L-(+)-threo-2-aminophenyl-1,3-propanediol, (−)-brucine, (+)-quinidine, (−)-quinine, (−)-cinchonidine, (+)-cinchonine, (+)-dehydroabietylamine, (+)-yohimbine, (−)-nicotine, (−)-ephedrine, (+)-ephedrine, (−)-N-methylephedrine, R(+)-1-phenylethylamine, S(−)-1-phenylethylamine, (+)-pseudoephedrine and (−)-α-phenyl-β-p-tolylethylamine. Among the above mentioned optically active bases, R(+)-1-phenylethylamine is particularly preferred. The reduction of S(−)-N-(2,6-dimethylphenyl)-alanine of the formula II to S(−)-N-(1'-methyl-2'-hydroxyethyl)-2,6-dimethylaniline of the formula III is conveniently carried out in an inert solvent. Examples of suitable inert solvents are aliphatic and aromatic hydrocarbons and, in particular, ethers. Specific examples of suitable solvents are hexane, cyclohexane, benzene, toluene, diethyl ether, tetrahydrofuran and dioxan.

Suitable reducing agents are lithium aluminium hydride and, in particular, borane. It is preferred to use borane in the form of a complex, especially as borane-dimethyl sulfide complex or as borane-tetrahydrofuran complex. The reducing agent is normally employed in stoichiometric amount up to an excess of 100%, based on the stoichiometric amount. The reaction temperature may be between 10° C. and the boiling point of the reaction mixture.

The conversion of S(−)-N-(1'-methyl-2'-hydroxyethyl)-2,6-dimethylaniline of the formula III into S(+)-N-(1'-methyl-2-hydroxyethyl)-N-chloroacetyl-2,6-dimethylaniline of the formula IV is carried out by reaction with a chloroacetylating agent such as chloroacetyl chloride or chloroacetic anhydride, in the presence of a base, in an inert solvent. Suitable bases are in particular alkali metal carbonates and bicarbonates, as well as tertiary amines such as triethylamine and pyridine. Suitable inert solvents are hydrocarbons such as hexane, cyclohexane, benzene, toluene and chlorobenzene. The chloroacetylating agent may be used in stoichiometric amount or in a small excess. In practice, molar ratios of S(−)-N-(1'-methyl-2'-hydroxyethyl)-2,6-dimethylaniline of the formula III to chloroacetylating agent of 1:1 to 1:0.95 have proved suitable. The reaction is carried out with cooling or at moderately elevated temperature. The temperature range from 0° to 50° C. has proved particularly suitable. The etherification of the 2'-hydroxy group of the S(+)-N-(1'-methyl-2'-hydroxyethyl)-N-chloroacetyl-2,6-dimethylaniline of the formula IV may be advantageously be carried out by heating the substance, in the presence of a strong acid, in absolute methanol at reflux temperature. Suitable strong acids for the reaction are in particular sulfuric acid and p-toluenesulfonic acid, which may be used in an amount of 0.1 to 0.3 mole per mole of S(+)-N-(1'-methyl-2'-hydroxyethyl)-N-chloroacetyl-2,6-dimethylaniline of the formula IV. The etherification may conveniently be carried out in the presence of a hydrophilic agent, especially a ketal such as 2,2-dimethoxypropane. An equimolar amount or an excess of the hydrophilic agent is employed.

The S(−)-N-(1'-methyl-2'-methoxyethyl)-N-chloroacetyl-2,6-dimethylaniline obtainable by the process of this invention has an optical purity of 98% according to $^1$H-NMR spectroscopy with chiral Schiff reagents Europium-tris-(3-trifluoromethyl-hydroxymethylene)-d-campher. Compared with the known mixture of diastereoisomers of N-(1'-methyl-2'-methoxyethyl)-N-chloroacetyl-2,6-dimethylaniline, it has a markedly superior herbicidal action against weeds while not having increased phytotoxicity towards cultivated plants. It may therefore be formulated in known manner to herbicidal compositions and used for controlling weeds in cultivated plants.

In this description, the absolute configuration has been named in accordance with "Experientia", Vol. 12, pp. 81–94 (1956). The invention also relates to herbicidal compositions which contain active enantiomer of the formula I, as well as to methods of preemergent and postemergent weed control.

The compositions of this invention may be formulated in conventional manner and are prepared in a manner known per se by mixing and grinding optically active compounds of the formula I with suitable carriers, with or without the addition of dispersants and solvents. In this manner, dusts, tracking agents, granular formulations, wettable powders, pastes, emulsions, emulsifiable concentrates or solutions are prepared by known methods.

The rates of application for controlling weeds are normally from 0.1 to 10 kg of active ingredient per hectare, preferably 0.25 to 5 kg/ha.

The herbicidal activity of the S(−)-N-(1'-Methyl-2'-methoxyethyl)-N-chloroacetyl-2,6-dimethylaniline according to this invention is superior to that of the racemate.

Compared with the known racemic mixture, the S(−) isomer of N-(1'-methyl-2'-methoxyethyl)-N-chloroacetyl-2,6-dimethylaniline of this invention shows increased activity against the following species of weeds: *Avena fatua* (wild oats), *Cyperus esculentus, Amaranthus retroflexus, Galium aparine* and *Solanum nigrum*. Suprising, and of great improtance, is the good action against *Cyperus esculentus* Echinochloa and *Digitaria setaria*. These ubiquitous weeds are resistant to most herbicides and are therefore at present counted among the problem weeds. These weeds can be controlled in crops of useful plants with S(−)-N-(1'-methyl-2'-methoxyethyl)-N-chloroacetyl-2,6-dimethylaniline at exceedingly low rates of application.

The following Examples illustrate in more detail the preparation of the isomer of N-(1'-methyl-2'-methoxyethyl)-N-chloroacetyl-2,6-dimethylaniline having a S(−) configuration according to this invention. Temperatures are given in centigrade, parts and percentages are by weight.

EXAMPLE 1

Preparation of racemic N-(2,6-dimethylphenyl)-alanine

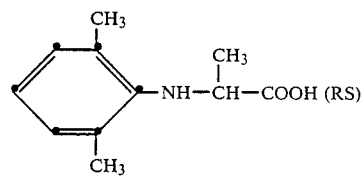

(a) N-(2,6-Dimethylphenyl)-alanine-methyl-ester

A 4.5 l sulfonating flask is charged with 745 ml (6 moles of 2,6-Dimethylaniline, 555 g (6.6 moles) of NaHCO$_3$ and 2007 ml (18 moles) of methyl 2-bromopropionate. The mixture is stirred and slowly heated for 1 hour to 120°–125° C. bath temperature while passing in nitrogen. Stirring is continued for 18 hours at this temperature accompanied by evolution of CO$_2$ and the mixture turns dark. After it has cooled, the reaction mixture is poured into 3 liters of ice-water and extracted portionwise with ethyl acetate. The ethyl acetate fractions are dried over sodium sulfate and concentrated in a rotary evaporator at 40° C. Excess methyl-2-bromopropionate is stripped off in vacuo and the residue is subjected to fractional distillation over a metal-coated 60 cm Vigreux column, affording 990.3 g of ester with a boiling point of 133°–134° (13 mbar).

(b) N-(2,6-Dimethylphenyl)-alanine 2232 g (10.78 moles) of the above ester and 6.6 l (2 moles/l) of sodium hydroxide solution are stirred at room temperature. The reaction temperature rises slowly to 36°. After 6 hours the emulsion has become a solution, in which no more starting material is present (analysis by gas chromatography) while stirring and cooling (to 0°–5° C.), the alkaline solution is adjusted to pH 3.5 with concentrated hydrochloric acid. The acid precipitates in the form of an oil, which crystallises after prolonged stirring. The resulting suspension is extracted with several portions of ethyl/acetate. The organic phase is washed with water and dried over sodium sulfate. The ethyl acetate is removed by distillation affording the racemic acid as solid residue, which is recrystallized from cyclohexane. Yield 1842 g, melting point 86°–89°.

(2) Cleaving of racemic N-(2,6-dimethylphenyl)-alanine with R(+)-1-phenylethylamine 625 ml (4.77 moles) of R(+)-1-phenylethylamine are added slowly to a stirred solution of 921 g (4.77 moles) of racemic N-(2,6-Dimethylphenyl)-alanine in 3.7 l of diisopropylether. The reaction temperature rises thereby to 45°. The salt begins to crystallise out after a short time. The batch is left to stand overnight, then the precipitate is isolated by filtration and washed with diisopropyl ether. The filter cake is recrystallised alternatively from ethyl acetate and acetonitrile until melting point and rotation are constant. Yield: 342 g of phenylethylamine salt with a melting point of 148°–150°; $[\alpha]_D^{20} = -16 \pm 1°$ (c=1.425% weight/volume in ethanol). 342 g (1.088 moles) of this salt are suspended in 2.5 l of ethyl acetate and 272 ml (1.088 moles (4 moles/l)) of hydrochloric acid is added thereto under vigorous stirring. After 10 minutes, the organic phase is separated washed with water and saturated saline solution, dried over sodium sulfate and concentrated. The crystalline residue is recrystallised twice with benzene and once from n-hexanol with the addition of charcoal. Thus 140 g of S(−)-(2,6-dimethylphenyl)alanine are obtained, m.p. 91°–93° $[\alpha]_D^{20} = -9 \pm 1°$ (c=1.325% weight/volume in ethanol).

3. Preparation of S(−)-N-(1′-methyl-2′-hydroxyethyl)-2,6-dimethylaniline

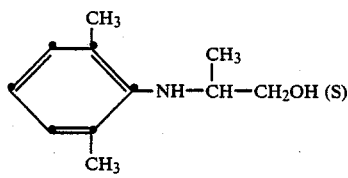

A solution of 168.3 (0.871 moles) of S(−)-N-(2,6-dimethylphenyl)-alanine in 1500 ml of anhydrous tetrahydrofuran is heated to reflux with the exclusion of moisture and while introducing dry $N_2$. Then 166 ml (1.66 moles) of borane-dimethyl sulfide complex are added very slowly dropwise, whereupon evolution of $H_2$ commences immediately. The reaction mixture is stirred under reflux for 20 hours and then cooled to 5° C. and methanol is added dropwise until the evolution of hydrogen ceases. The reaction mixture is concentrated in vacuo and the oily residue is taken up in ether and the ethereal solution is extracted portionswise with a total amount of 600 ml (2 moles/l) of hydrochloric acid. The aqueous hydrochloric acid phases are combined, adjusted to pH 8 with concentrated sodium hydroxide solution while cooling with ice, and extracted with ether. The ethereal fraction is washed with water, dried and concentrated. The residue is distilled in a high vacuum, affording 130.1 g of S(−)-N-(1′-methyl-2′-hydroxyethyl)-2,6-dimethylaniline with a boiling point of 95°–96° ($10^{-3}$ mbar); $[\alpha]_{365}^{20} = -13°$ (c=1.767% weight/volume in methanol).

4. Preparation of S(+)-N-(1′-methyl-2-hydroxyethyl-N-chloroacetyl-2,6-dimethylaniline

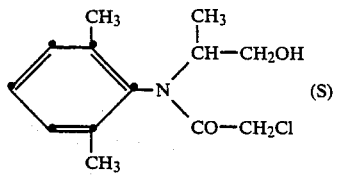

103 g (0.547 moles) of S(−)-N-(1′-methyl-2′-hydroxyethyl)-2,6-dimethylaniline are mixed with 58 g (0.547 moles) of sodium carbonate in 1 l of benzene. With efficient stirring, 43.6 ml (0.547 moles) of chloroacetyl chloride, dissolved in 50 ml of benzene, are slowly added dropwise thereto. The reaction mixture is then stirred for 2 hours at room temperature and then filtered. The benzene filtrate is diluted with ethyl acetate and extracted in a separating funnel, washed with water, (2 moles/l) hydrochloric acid, 10% sodium bicarbonate solution and saturated sodium chloride solution. The organic phase is dried over sodium sulfate and concentrated in a rotary evaporator. The residual oil crystallizes from diisopropylether. Thus 111.2 g of S(+)-N-(1′-methyl-2′-hydroxyethyl)-N-chloroacetyl-2,6-dimethylaniline are obtained, melting point 58°–60°. $[\alpha]_{365}^{20} = +46°$ (c=2.247% weight/volume in Methanol).

5. Preparation of S(−)-N-(1′-methyl-2′-methoxyethyl)-N-chloroacetyl-2,6-dimethylaniline

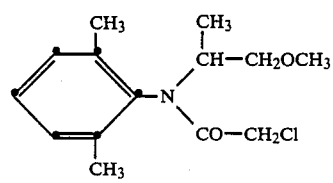

111.2 g (0.435 moles) of S(+)-N-(1′-methyl-2′-hydroxyethyl)-N-chloroacetyl-2,6-dimethylaniline are dissolved in 1.1 l of absolute methanol. Thereto is added 11.9 ml (0.2175 moles) of 98% sulfuric acid and the reaction mixture is heated under reflux for 15 hours. The solution is then concentrated in a rotary evaporator and the oily residue is taken up in ethyl acetate. The ethyl acetate solution is washed with water and with sodium bicarbonate solution. The organic solution is dried over sodium sulfate and concentrated in vacuo and the residue oil is subjected to fractional distillation in a high vacuum. Boiling point 118°–124° C./0.01 mbar, yield 90.9 g. The destillation product is recrystalized from benzine in dry-ice and yields 76.5 g of crystalline title product, which has a melting point of 27°–30° and a rotary index $[\alpha]_{365}^{20} = -39°$ (c=1.995% weight/volume in n-hexane). The optical purity is 98%.

EXAMPLE 2

The S(−)-isomer and the racemic mixture of N-(1′-methyl-2′-methoxyethyl)-N-chloroacetyl-2,6-dimethylaniline are compared in a herbicidal test in a greenhouse in order to determine the improved activity of the isomer. Both compounds are formulated to a 25% emulsifiable concentrate of the following composition:

25 parts of active ingredient
5 parts of a mixture of nonylphenol polyoxyethylene and calcium dodecylbenzene sulfonate
15 parts of cyclohexanone
55 parts of xylene.

This concentrate is then diluted with water to the desired concentration.

The herbicidal activity is determined as follows:

PREEMERGENCE HERBICIDAL ACTIVITY
(INHIBITION OF GERMINATION)

Plant seeds are sown in pots with a diameter of 12–15 cm in a greenhouse. Immediately afterwards, the surface of the soil is treated with an aqueous emulsion of the test compounds, obtained from the emulsifiable concentrate. A range of concentrations is employed and the amount of active ingredient applied is in the range from 2 kg to 32 g per hectare. The pots are then kept in the greenhouse at a temperature of 22°–25° C. and at 50–70% relative humidity. The test is evaluated after 3 weeks and the results are expressed in accordance with the following rating:
1 = plants have not germinated or are totally withered
2–3 = very pronounced activity
4–6 = average activity
7–8 = slight activity
9 = no activity (as untreated controls).

The results are reported in the following table.

test compound corresponds to a rate of application of 1 and 2 kg per hectare respectively. The average growth of the grasses is measured 21 days after application and compared to that of a not-treated grass-mixture (=100% growth).

The compounds tested are:
N-(1-methyl-2′-methoxyethyl)-chloroacetyl-2,6-dimethylaniline S(−)-isomer,

|  | S(−)-isomer | | | | | | | racemate | | | | | | |
|---|---|---|---|---|---|---|---|---|---|---|---|---|---|---|
|  | application rate g/ha | | | | | | | | | | | | | |
| plant | 2000 | 1000 | 500 | 250 | 125 | 63 | 32 | 2000 | 1000 | 500 | 250 | 125 | 63 | 32 |
| monocotyledones | | | | | | | | | | | | | | |
| barley | 3 | 4 | 4 | 6 | 9 | 9 | 9 | 4 | 5 | 7 | 9 | 9 | 9 | 9 |
| wheat | 3 | 4 | 6 | 9 | 9 | 9 | 9 | 6 | 7 | 9 | 9 | 9 | 9 | 9 |
| corn | 5 | 6 | 7 | 7 | 8 | 9 | 9 | 5 | 7 | 8 | 9 | 9 | 9 | 9 |
| millet | 1 | 3 | 3 | 6 | 7 | 9 | 9 | 2 | 3 | 4 | 7 | 9 | 9 | 9 |
| rice | 1 | 1 | 2 | 3 | 8 | 8 | 8 | 2 | 3 | 3 | 4 | 6 | 8 | 9 |
| *Avena fatua* | 3 | 5 | 8 | 9 | 9 | 9 | 9 | 7 | 7 | 9 | 9 | 9 | 9 | 9 |
| *Bromus tectorum* | 1 | 2 | 2 | 3 | 3 | 9 | 9 | 1 | 1 | 2 | 2 | 3 | 6 | 9 |
| *Lolium perenne* | 1 | 2 | 2 | 2 | 4 | 7 | 9 | 1 | 2 | 2 | 4 | 9 | 9 | 9 |
| *Alopecurus myos.* | 2 | 5 | 6 | 9 | 9 | 9 | 9 | 3 | 3 | 6 | 9 | 9 | 9 | 9 |
| *Digitaria sang.* | 1 | 1 | 2 | 2 | 2 | 3 | 3 | 1 | 1 | 1 | 2 | 2 | 4 | 8 |
| *Echinochloa grus calli* | 1 | 1 | 1 | 1 | 2 | 3 | 3 | 1 | 1 | 2 | 2 | 3 | 4 | 4 |
| *Sorghum halepense* | 1 | 1 | 1 | 4 | 4 | 5 | 5 | 1 | 1 | 1 | 4 | 4 | 7 | 9 |
| *Rottboellia exaltata* | 3 | 5 | 7 | 8 | 9 | 9 | 9 | 3 | 7 | 8 | 9 | 9 | 9 | 9 |
| *Cyperus esculentus* | 1 | 1 | 3 | 3 | 3 | 5 | 8 | 2 | 2 | 3 | 4 | 6 | 9 | 9 |
| *Poa trivialis* | 1 | 1 | 2 | 3 | 4 | 6 | 7 | 1 | 2 | 2 | 3 | 7 | 8 | 9 |
| *Setaria glauca* | 1 | 1 | 1 | 1 | 2 | 3 | 3 | 1 | 1 | 1 | 2 | 3 | 8 | 9 |
| *Setaria italica* | 1 | 1 | 1 | 1 | 2 | 3 | 3 | 1 | 1 | 1 | 1 | 2 | 4 | 5 |
| *Pennisetum glaucum* | 1 | 1 | 1 | 1 | 4 | 8 | 9 | 1 | 1 | 2 | 2 | 6 | 7 | 8 |
| *Festuca ovina* | 1 | 1 | 1 | 1 | 5 | 6 | 6 | 1 | 1 | 1 | 2 | 5 | 8 | 9 |
| dicotyledones | | | | | | | | | | | | | | |
| soya-bean | 6 | 7 | 8 | 8 | 9 | 9 | 9 | 7 | 8 | 9 | 9 | 9 | 9 | 9 |
| rape (colza) | 8 | 9 | 9 | 9 | 9 | 9 | 9 | 9 | 9 | 9 | 9 | 9 | 9 | 9 |
| cotton | 5 | 7 | 8 | 9 | 9 | 9 | 9 | 6 | 8 | 8 | 9 | 9 | 9 | 9 |
| sugar-beet | 4 | 7 | 8 | 9 | 9 | 9 | 9 | 7 | 8 | 9 | 9 | 9 | 9 | 9 |
| *Abutilon sp.* | 2 | 4 | 7 | 8 | 9 | 9 | 9 | 5 | 6 | 9 | 9 | 9 | 9 | 9 |
| *Sida spinosa* | 2 | 3 | 3 | 4 | 5 | 7 | 8 | 3 | 4 | 4 | 6 | 7 | 8 | 9 |
| *Xanthium sp.* | 9 | 9 | 9 | 9 | 9 | 9 | 9 | 8 | 8 | 8 | 9 | 9 | 9 | 9 |
| *Amaranthus retroflexus* | 1 | 1 | 1 | 1 | 1 | 2 | 4 | 1 | 1 | 1 | 1 | 2 | 4 | 8 |
| *Chenopodium album* | 1 | 3 | 4 | 6 | 8 | 9 | 9 | 2 | 2 | 7 | 7 | 8 | 9 | 9 |
| *Ipomoea purpurea* | 4 | 5 | 6 | 7 | 8 | 9 | 9 | 5 | 6 | 7 | 8 | 9 | 9 | 9 |
| *Sinapis alba* | 3 | 7 | 9 | 9 | 9 | 9 | 9 | 6 | 9 | 9 | 9 | 9 | 9 | 9 |
| *Stellaria media* | 1 | 4 | 8 | 8 | 9 | 9 | 9 | 2 | 9 | 9 | 9 | 9 | 9 | 9 |
| *Chrysanthemum leucum* | 1 | 6 | 9 | 9 | 9 | 9 | 9 | 3 | 7 | 9 | 9 | 9 | 9 | 9 |
| *Galium aparine* | 2 | 3 | 9 | 9 | 9 | 9 | 9 | 4 | 5 | 9 | 9 | 9 | 9 | 9 |
| *Viola tricolor* | 2 | 2 | 3 | 3 | 9 | 9 | 9 | 3 | 4 | 4 | 6 | 6 | 9 | 9 |
| *Veronica sp.* | 1 | 1 | 1 | 1 | 1 | 1 | 9 | 1 | 1 | 1 | 1 | 2 | 9 | 9 |
| *Leptochloa imbricata* | 1 | 1 | 1 | 1 | 1 | 3 | 3 | 1 | 1 | 1 | 1 | 1 | 4 | 5 |
| *Portulacca* | 1 | 1 | 1 | 3 | 9 | 9 | 9 | 1 | 1 | 5 | 7 | 9 | 9 | 9 |
| *Solanum nigrum* | 1 | 2 | 3 | 3 | 6 | 8 | 9 | 2 | 2 | 6 | 6 | 6 | 7 | 8 |

The optically active isomer shows improved herbicidal activity as compared with the racemate against the weeds, which are listed with their latin names, while the tolerance of both substance towards the culture plants is about the same (marks 7 to 9).

EXAMPLE 3

Growth inhibition of grasses

A mixture of seeds of the grasses *Lolium perenne, Poa pratensis, Festuca ovina,* and *Cynodon dactylon* is sown into plastic dishes filled with an earth/peat/sand mixture (6:3:1), in a greenhouse, and watered as required. The emergent grasses are cut back weekly to a height of about 4 cm and, about 50 days after sowing and 1 day after the last cut, are sprayed with aqueous spray mixture of the compound to be tested. The concentration of N-(1-methyl-2′-methoxyethyl)-chloroacetyl-2,6-dimethylaniline, racemate.

The results are as follows:

| application rate | 1 kg/ha | 2 kg/ha |
|---|---|---|
| S(−)-isomer | 24% | 17% |
| racemate I | 27% | 17% |

EXAMPLE 4

Growth inhibition of cereals

Summar barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration corresponds to 2, 1 and 0.5 kg respectively of active ingredient per hectare. The growth of the cereals is measured 28 days after application. A comparison with untreated controls shows that the growth of cereal plants treated with the S(—)-isomer according to the invention is substantially reduced.

The results are as follows:

| application rate | 0.5 kg/ha | 1 kg/ha | 2.5 kg/ha |
|---|---|---|---|
| rye: | | | |
| S(—)-isomer | 51% | 51% | 8% |
| racemate | 72% | 62% | 10% |
| barley | | | |
| S(—)-isomer | 44% | 16% | 11% |
| racemate | 56% | 33% | 18% |

EXAMPLE 5

Selective herbicidal activity against the notorious rice weed *Echinochloa crus galli* in paddy-rice Twenty-five-day-old rice plants are transplanted into large rectangular plastic containers measuring 25×17 cm² and 12 cm high in the greenhouse. Seeds of the weed *Echinochloa crus galli* were then sown between the rows of rice plants. The containers were well watered and kept at a temperature of about 25° C. and at high humidity. Twelve days later, when the weeds have emerged and reached the 2–3 leaf stage, the soil in each of the containers was covered with a layer of water to a height of 2.5 cm. The active substance was then applied in the form of an emulsion concentrate with a pipette between the rows of plants. The emulsifiable concentrate is diluted and applied so that it corresponds to a field application rate of 0.5, 0.25 and 0.125 kg of active substance per hectare. The test was evaluated 4 weeks later. The results in the table below show that the S(—)-isomer is more tolerant towards rice and has better herbicidal action against *Echinochloa crus galli* than the racemate.

| application rate | Compound | | | | | |
|---|---|---|---|---|---|---|
| | S(—)-isomer | | | racemate | | |
| kg/ha | $\frac{1}{2}$ | $\frac{1}{4}$ | $\frac{1}{8}$ | $\frac{1}{2}$ | $\frac{1}{4}$ | $\frac{1}{8}$ |
| rice | 6 | 7 | 9 | 2 | 4 | 7 |
| Echinochloa | 1 | 1 | 1 | 2 | 2 | 3 |

What is claimed is:

1. The method of selectively combating *Echinochloa crus galli* in rice crops under flooded conditions which comprises applying post-emergently to said crops or the environs of their growth S(—)-(1'-methyl-2'-methoxyethyl)-N-chloroacetyl-2,6-dimethylaniline, substantially free of its R anantiomer, at a rate of from about 0.125 to about 0.5 kg/ha.

* * * * *